(12) United States Patent
Funk et al.

(10) Patent No.: US 10,039,630 B2
(45) Date of Patent: Aug. 7, 2018

(54) IMPLANT CONTAINER AND IMPLANT CONTAINER SYSTEM

(75) Inventors: Peter Funk, Ostelsheim (DE); Thilo Jendreck, Emmendingen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 1578 days.

(21) Appl. No.: 13/597,918

(22) Filed: Aug. 29, 2012

(65) Prior Publication Data
US 2013/0220858 A1    Aug. 29, 2013

(30) Foreign Application Priority Data

Aug. 31, 2011    (EP) ..................... 11007075

(51) Int. Cl.
| | |
|---|---|
| A61B 17/06 | (2006.01) |
| A61F 2/00 | (2006.01) |
| A61B 50/20 | (2016.01) |
| A61B 17/80 | (2006.01) |
| A61B 50/00 | (2016.01) |
| A61B 50/30 | (2016.01) |

(52) U.S. Cl.
CPC ............ *A61F 2/0095* (2013.01); *A61B 50/20* (2016.02); *A61B 17/80* (2013.01); *A61B 17/8061* (2013.01); *A61B 2050/0059* (2016.02); *A61B 2050/3008* (2016.02)

(58) Field of Classification Search
CPC .......... B65D 43/20; B65D 43/16; B65D 1/24; B65D 2543/00444; B65D 2583/0468; B65D 2583/0486; B65D 5/723; B65D 2583/0454; B65D 5/68; B65D 21/086; A61F 2/0095; A61B 50/20; A61B 2050/3008; A61B 2050/0059; A61B 17/8061; A61B 17/80
USPC ....... 206/438, 467, 468, 774, 756, 570, 564, 206/572, 338, 339, 341, 363, 370, 372, 206/758; 220/345.3, 345.1, 526, 523, 220/812, 811, 810, 8
See application file for complete search history.

(56) References Cited

U.S. PATENT DOCUMENTS

| | | | | |
|---|---|---|---|---|
| 2,164,832 | A | * | 7/1939 | Nitardy .............. B65D 83/0481 206/534.1 |
| 2,502,311 | A | * | 3/1950 | Clarke ............... B65D 83/0409 221/246 |

(Continued)

FOREIGN PATENT DOCUMENTS

| | | |
|---|---|---|
| DE | 672631 C | 3/1939 |
| DE | 924474 C | 3/1955 |

(Continued)

*Primary Examiner* — Jacob K Ackun
*Assistant Examiner* — Jenine Pagan
(74) *Attorney, Agent, or Firm* — Lerner, David, Littenberg, Krumholz & Mentlik, LLP

(57) ABSTRACT

An implant container for accommodating one or more bone plate implants has a base having a receiving structure configured to receive at least one bone plate implant so that the bone plate implant is held in a defined relationship relative to the base. A lid of the implant container has an opening and is movable relative to the base from a first position to at least a second position. In the first position the lid covers the receiving structure at least partially so as to prevent implant removal, whereas in the second position the lid provides access to the receiving structure via the opening so as to permit implant removal.

22 Claims, 9 Drawing Sheets

(56) References Cited

U.S. PATENT DOCUMENTS

| | | | | |
|---|---|---|---|---|
| 2,645,336 | A | * | 7/1953 | Waber ............... B65D 83/0409 206/540 |
| 2,777,570 | A | * | 1/1957 | Mytinger ................ A61J 1/03 206/539 |
| 2,792,934 | A | * | 5/1957 | Rocchetti ............... B25H 3/003 206/379 |
| 3,397,770 | A | * | 8/1968 | Howard ................ B65D 11/12 206/539 |
| 4,153,160 | A | * | 5/1979 | Leigh .................... A61B 50/33 206/370 |
| 4,564,270 | A | | 1/1986 | Willie |
| 4,572,376 | A | * | 2/1986 | Wrennall ................ A61J 7/04 206/534 |
| 4,597,765 | A | | 7/1986 | Klatt |
| 4,697,703 | A | | 10/1987 | Will |
| 4,750,619 | A | | 6/1988 | Cohen et al. |
| 4,941,570 | A | * | 7/1990 | Kruger ................ B25H 3/003 206/267 |
| 4,966,599 | A | | 10/1990 | Pollock |
| 5,178,267 | A | | 1/1993 | Grabenkort et al. |
| 5,193,679 | A | | 3/1993 | White |
| 5,257,692 | A | | 11/1993 | Heacox |
| 5,379,895 | A | | 1/1995 | Foslien |
| 5,394,983 | A | * | 3/1995 | Latulippe ............... A61L 2/26 206/370 |
| 5,405,005 | A | | 4/1995 | White |
| 5,494,162 | A | * | 2/1996 | Treace ................ A61F 2/0095 206/438 |
| 5,568,865 | A | | 10/1996 | Mase et al. |
| 5,611,426 | A | * | 3/1997 | Warfield ............ B65D 5/4204 206/308.1 |
| 5,664,408 | A | | 9/1997 | Chesterfield et al. |
| 5,690,223 | A | * | 11/1997 | Wood ........................ A61L 2/26 206/363 |
| 5,690,226 | A | | 11/1997 | N'Guyen |
| 5,720,391 | A | | 2/1998 | Dohm et al. |
| 5,868,253 | A | | 2/1999 | Krueger et al. |
| 6,039,183 | A | | 3/2000 | Rudnick et al. |
| 6,161,695 | A | | 12/2000 | Nicolais |
| 6,622,864 | B1 | | 9/2003 | Debbs et al. |
| 6,830,149 | B2 | | 12/2004 | Merboth et al. |
| 6,863,692 | B2 | | 3/2005 | Meulink |
| 6,896,138 | B2 | * | 5/2005 | Rock .................... B65D 75/327 206/531 |
| 2002/0029981 | A1 | | 3/2002 | Nigam |
| 2003/0033016 | A1 | | 2/2003 | Dees |
| 2003/0070944 | A1 | | 4/2003 | Nigam |
| 2005/0033430 | A1 | * | 2/2005 | Powers ............. A61B 17/7059 623/17.11 |
| 2007/0034538 | A1 | | 2/2007 | Landis |
| 2007/0095689 | A1 | * | 5/2007 | Pratt ...................... A61B 50/30 206/366 |
| 2010/0065456 | A1 | | 3/2010 | Junk et al. |
| 2010/0069969 | A1 | * | 3/2010 | Ampuero ........... A61B 17/8605 606/301 |
| 2011/0155592 | A1 | | 6/2011 | Liccardo et al. |
| 2011/0163155 | A1 | * | 7/2011 | Kalin ...................... A61J 1/03 229/122 |
| 2012/0191203 | A1 | | 7/2012 | Liccardo et al. |

FOREIGN PATENT DOCUMENTS

| | | |
|---|---|---|
| DE | 3016606 A1 | 11/1981 |
| DE | 8911659 U1 | 11/1989 |
| DE | 9312355 U1 | 10/1993 |
| DE | 20204334 U1 | 8/2002 |
| DE | 102007016537 A1 | 10/2008 |
| EP | 0133753 A2 | 3/1985 |
| EP | 0467814 A1 | 1/1992 |
| GB | 2418421 A | 3/2006 |
| WO | 03079918 A1 | 10/2003 |

\* cited by examiner

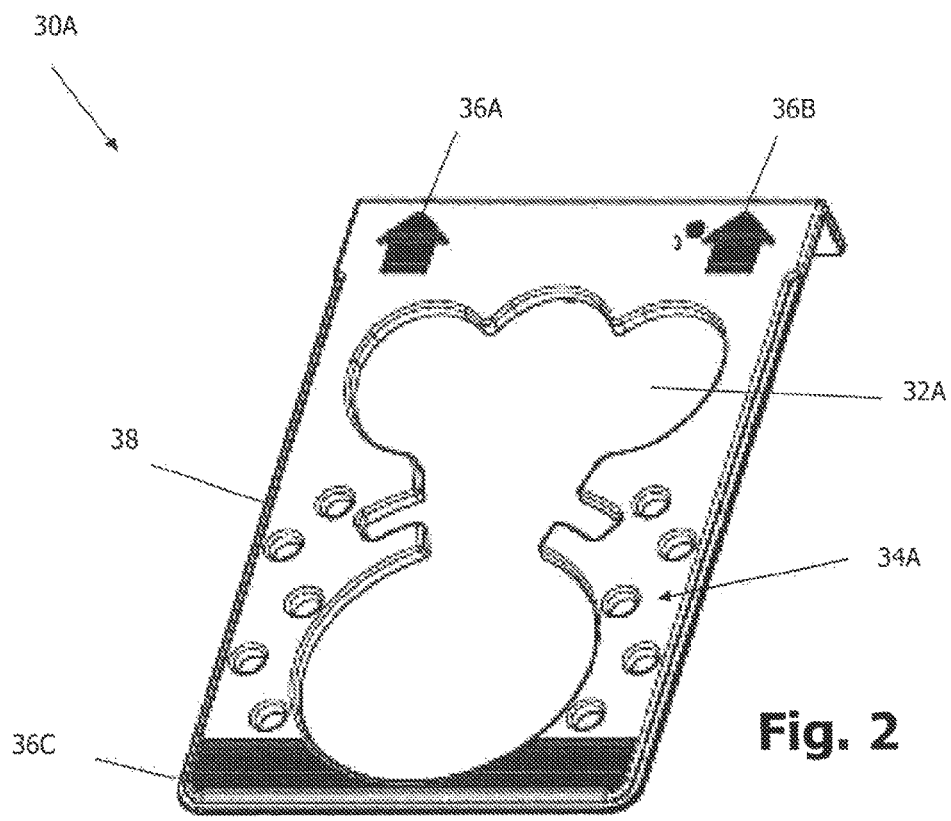
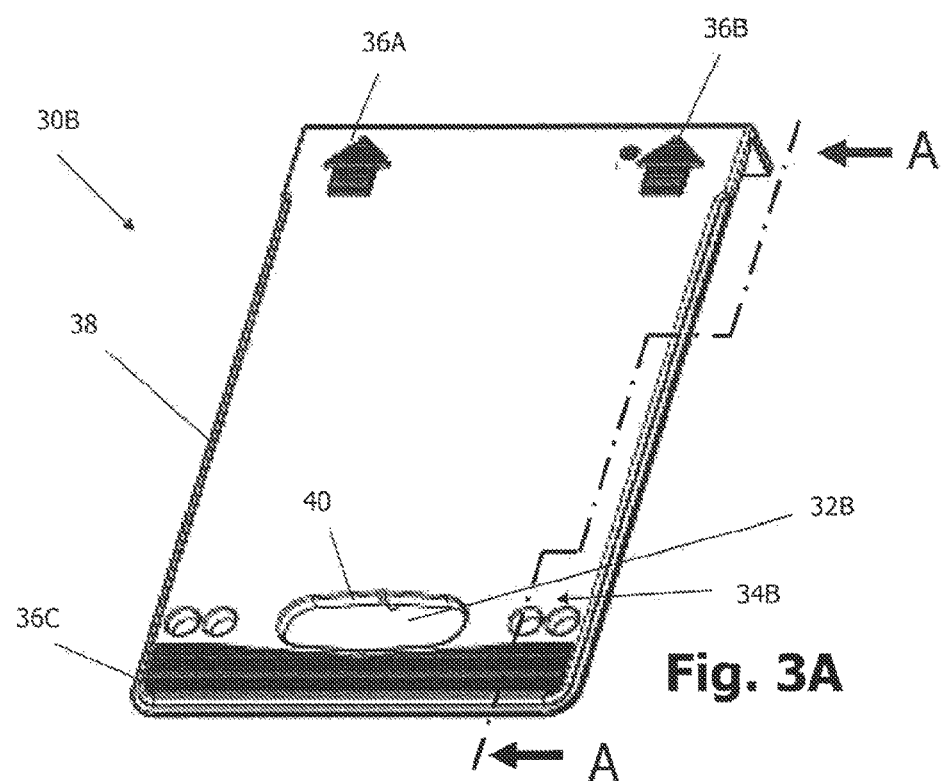

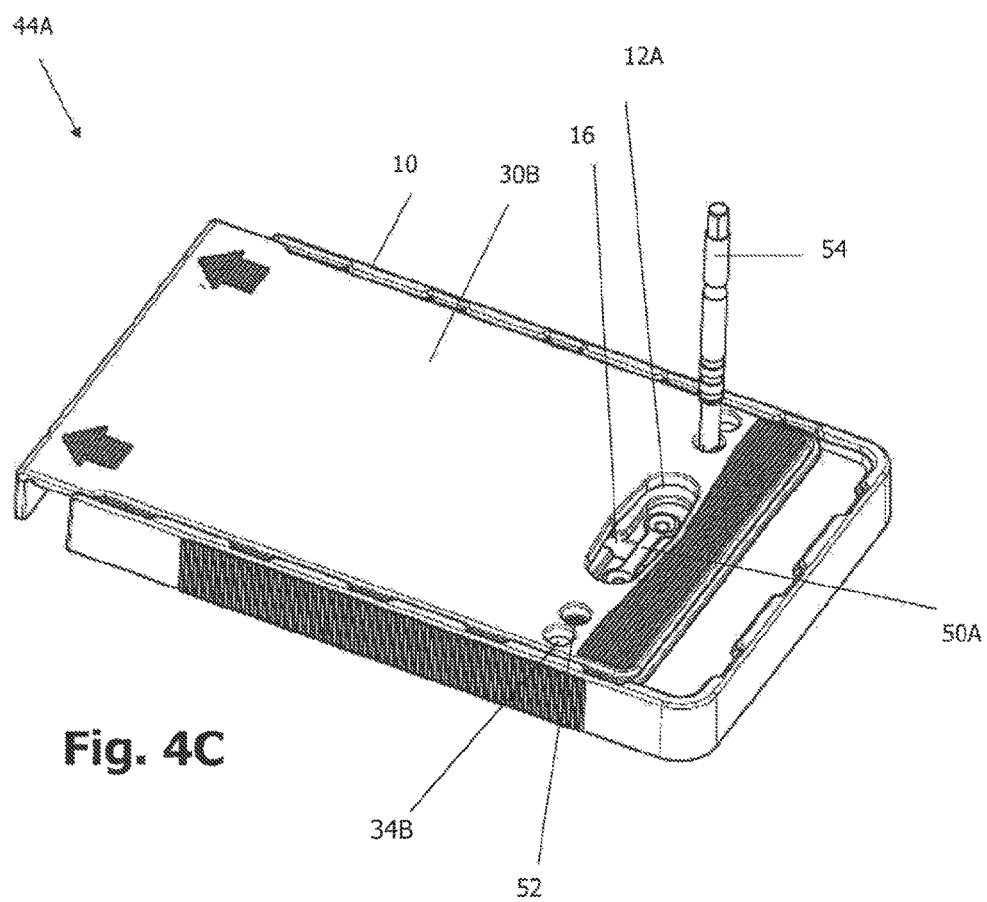

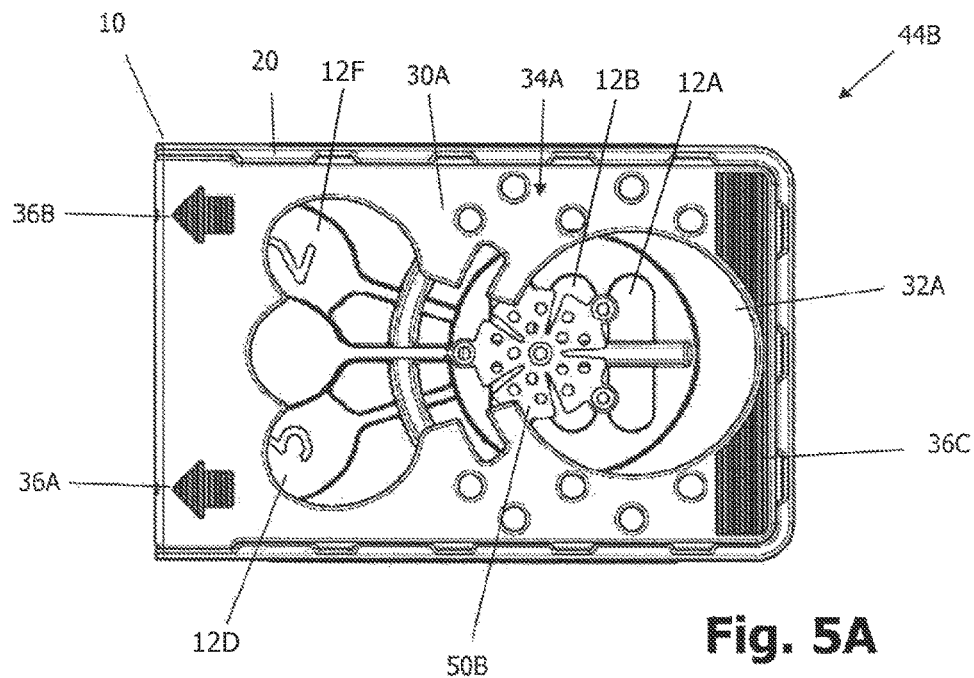
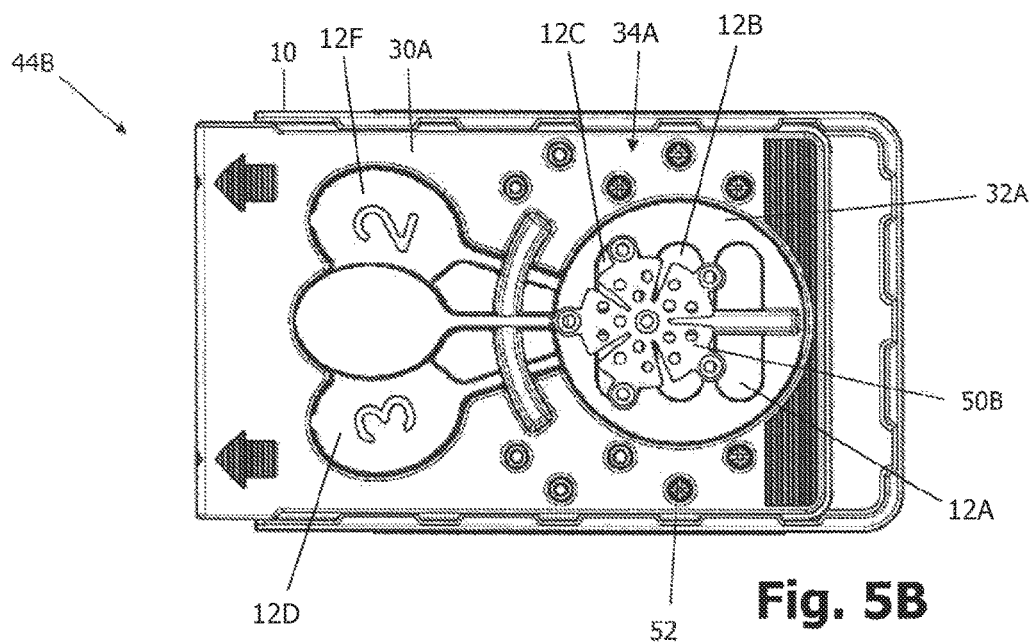

IMPLANT CONTAINER AND IMPLANT CONTAINER SYSTEM

CROSS-REFERENCE TO RELATED APPLICATION

The present application claims priority from European Patent Application No. 11007075.2 filed Aug. 31, 2011, the disclosure of which is hereby incorporated herein by reference.

BACKGROUND OF THE INVENTION

The present disclosure generally relates to the field of surgical implants. In particular, an implant container for receiving a bone plate implant is described. Also described are systems comprising the implant container.

Bone plate implants are widely used to treat bone fractures, to re-attach a previously removed piece of bone and for other purposes. In many cases fixation elements such as bone screws or bone pins are used for fixing the bone plate implants to bone. During a surgical operation the fixation elements have to be conveniently held at the ready for use by a surgeon.

In this regard GB 2 418 421 A discloses a container for elongate surgical fixation elements. The container has a base in which circular holes are provided. The circular holes serve as receiving structures for the surgical fixation elements. Specifically, the surgical fixation elements are introduced with their shafts into the circular holes and are held therein in an upright (e.g., hanging or standing) position.

The container taught in GB 2 418 421 A has a sliding lid that closes an upper portion of the base. By sliding the lid in an open position, the surgeon obtains access to the fixation elements and may remove same from the base. In the case the fixation elements are realized as bone screws with screw heads, a screw driver having a tip that frictionally or magnetically engages the screw heads may be used for bone screw removal.

The lid of the container comprises a plurality of openings. The openings are permeable for a sterilization medium and permit a sterilization of the container (and, optionally, of the fixation elements accommodated therein). For the same purpose openings may also be provided in the base.

BRIEF SUMMARY OF THE INVENTION

There is a need for an implant container that facilitates the handling of bone plate implants in a surgical environment.

According to one aspect, an implant container for receiving at least one bone plate implant is provided, wherein the implant container comprises a base having a first receiving structure configured to receive at least one first bone plate implant so that the first bone plate implant is held in a defined relationship relative to the base, and a first lid having a first opening and being movable relative to the base from a first position to at least a second position, wherein in the first position the first lid covers the first receiving structure at least partially so as to prevent implant removal and in the second position the first lid provides access to the first receiving structure via the opening so as to permit implant removal.

The base may comprise one or more further receiving structures in addition to the first receiving structure. For example, the base may comprise at least one second receiving structure configured to receive at least one second bone plate implant so that the second bone plate implant is held in a defined relationship relative to the base. The second bone plate implant may be of the same type like the first bone plate implant or of a different type.

The first receiving structure and the second receiving structure may be provided in different, non-overlapping portions of the base. In another implementation, the first receiving structure and the second receiving structure may overlap at least partially.

In the second position the lid may provide access to the second receiving structure via one of the first opening and an optional second opening in the first lid so as to permit plant removal. In another realization, the first lid is movable relative to the base from the first position to a third position different from the second position. In such a realization the first lid may cover in the first position and in the second position the second receiving structure at least partially so as to prevent implant removal and, in a third position, the first lid may provide access to the second receiving structure via one of the first opening and an optional second opening so as to permit implant removal.

In addition or as an alternative to the second receiving structure, the base may comprise at least one third receiving structure configured to receive a fixation element for fixing the bone plate implant to bone. The fixation element may take the form of a bone screw, a bone peg or a bone pin.

In the first position the first lid may cover the third receiving structure at least partially so as to prevent removal of the fixation element and, in one of the second position and an optional fourth position, the first lid may provide access to the second receiving structure via one of the first opening and an optional third opening in the first lid so as to permit removal of the fixation element. As an example, in the second position access to both the first bone plate implant and one or more fixation elements for fixing the first bone plate implant to bone may be provided via a single opening or via different openings in the lid. In this way it can be ensured that the surgeon utilizes the intended fixation elements for bone plate implant fixation.

The third opening may be dimensioned so that walls in the first lid defining the third opening act as an axial guiding structure for a removal tool upon removal of the fixation element by the removal tool. As an example, the third opening may have a circular shape that has a slightly larger diameter than that of a tip and a shaft of the removal tool. The tip and the shaft of the removal tool can thus be guided by the third opening towards the fixation element held in the third receiving structure. The third receiving structure may, for example, be realized in the form of an aperture (e.g., a bore) as generally known from GB 2 418 421 A.

Depending on the surgical procedure in which the first or any other bone plate implant will be used, the bone plate implant may be configured to be fixed to bone via a plurality of fixation elements. In such a realization the base may comprise a number of third receiving structures and a first lid may comprise a number of third openings that correspond to the number of the plurality of fixation elements needed for bone plate implant fixation.

In one variant, the first lid is slidably guided relative to the base. In another variant, the first lid may be rotatably movable relative to the base.

The first receiving structure, and optionally any additional receiving structure, may be realized in the form of a recess in the base. A particular recess may substantially be shaped in accordance with at least a portion of a contour of the associated bone plate implant. In one realization, the recess prevents the bone plate implant from laterally moving relative to the base. In another realization, the recess may limit the movement of the bone plate implant relative to the base so as to still guarantee the defined relationship of the bone plate implant relative to the base.

A latching mechanism may be provided that predefines one or more of the positions (such as at least the second position) of the lid relative to the base. The lid may be configured to be moved from any position back to the first position (e.g., to close the implant container after implant removal).

The implant container may further comprise a packaging member configured to package at least the base, the first lid and the first bone plate implant in a sterile manner. The packaging member may comprise a blister pack. Additionally, or as an alternative, the packaging member may comprise a bag. If the bag is provided in addition to the blister pack, the blister pack may be included in the bag.

Of course, the implant container may also comprise the first bone plate implant. Furthermore, additional bone plate implants and/or one or more fixation elements may be comprised by the implant container.

The first lid may comprise a gripping structure arranged on a surface of the first lid that faces a way from the base or laterally on the first lid. The gripping structure is configured to facilitate a transfer of the first lid from the first position to at least the second position. Exemplary realizations of the gripping structure include a depression, a tab, a corrugation and so on. In addition or as an alternative to the gripping structure, the implant container may comprise a holding member arranged on a surface of the first lid that faces towards the base. The holding member is configured to hold at least the first bone plate implant in at least the first receiving structure. As such, the holding member may be realized in the form a rip, a bar or in any suitable form.

According to another aspect, an implant container system comprising the implant container presented herein is provided. The implant container system further comprises a second lid movable relative to the base from the first to one of the second position and an optional third position, wherein the second lid has a second opening and wherein in the first position the second lid covers the second receiving structure at least partially so as to prevent implant removal and, in one of the second position and the third position, the second lid provides access to the first receiving structure via the second opening so as to permit implant removal, wherein the base is configured to be selectively used in combination with one of the first lid and the second lid.

According to a still further aspect, an implant container system comprising the implant container presented herein as well as the removal tool is provided.

BRIEF DESCRIPTION OF THE DRAWINGS

In the following, exemplary realizations of the implant container and the implant container system presented herein are discussed in more detail with reference to the drawings, wherein:

FIG. 2 shows a perspective front view of a first embodiment of a lid for an implant container;

FIG. 3A shows a perspective front view of a second embodiment of a lid for an implant container;

FIG. 4C shows a perspective view of the implant container according to FIG. 4B in a surgical scenario with a removal tool;

FIG. 5A shows a top view of a second embodiment of an implant container in a first relative position between base and lid;

FIG. 5B shows a top view of the implant container of FIG. 5A and a second relative position between base and lid;

DETAILED DESCRIPTION

Figure 1A:
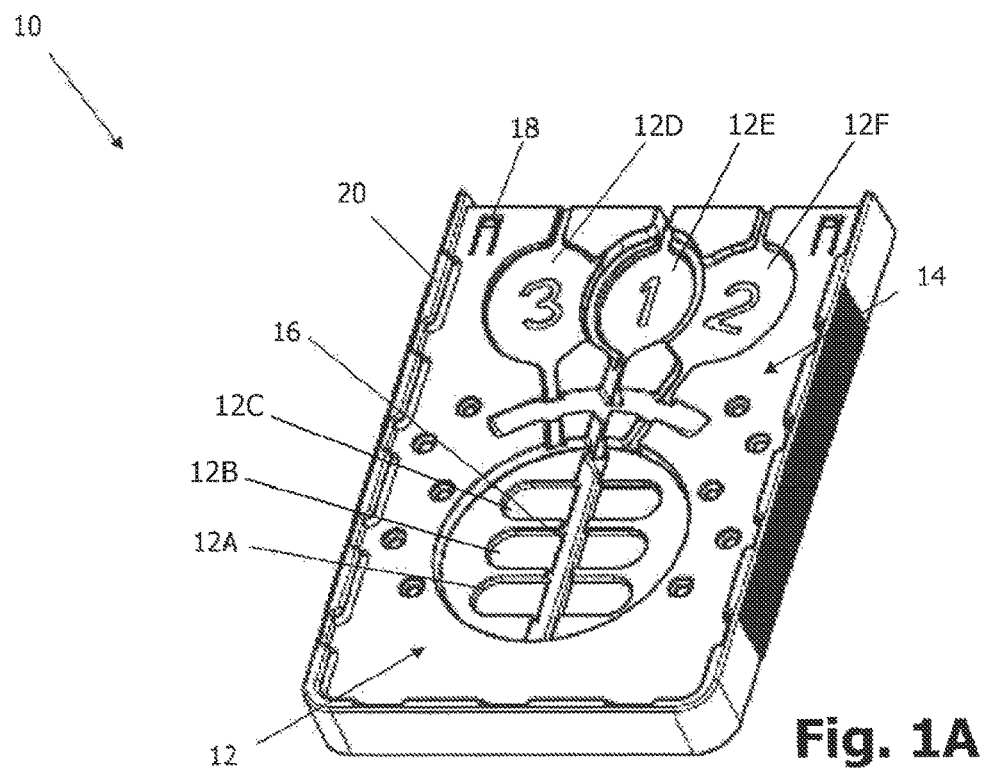
FIG. 1A shows a perspective front view of an embodiment of a base for an implant container.

In the following various embodiments of implant containers and implant container systems will be presented. The same reference numerals will be used to denote the same or similar structures in the drawings.

Figure 1B:
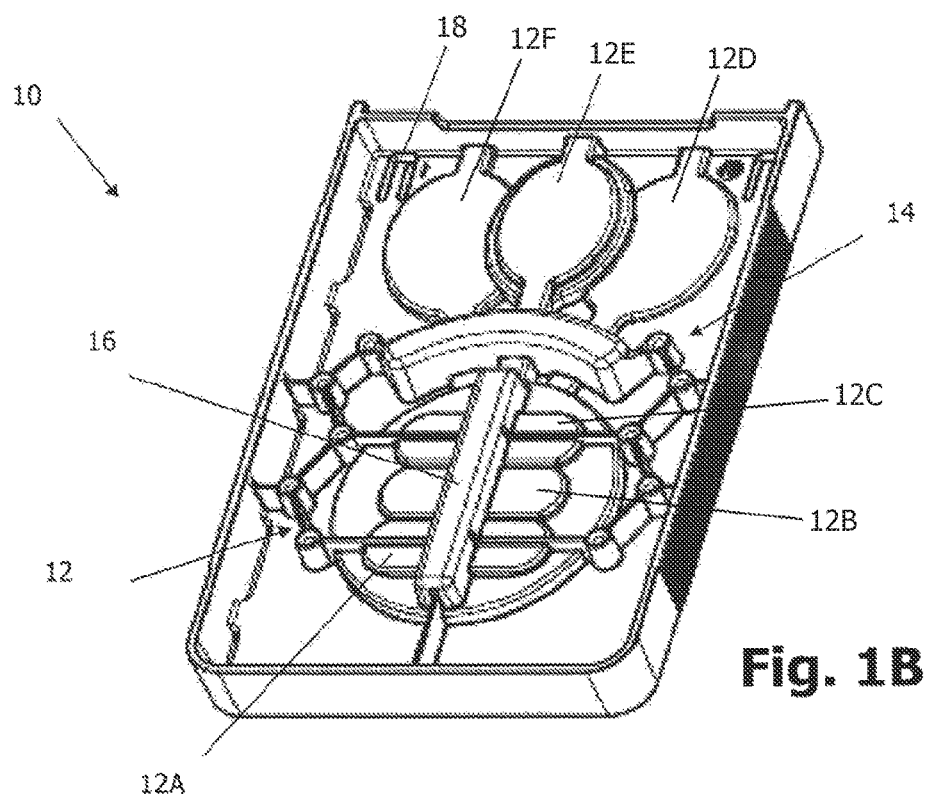
FIG. 1B shows a perspective back view of the base of FIG. 1A.

FIGS. 1A and 1B show a perspective front and back view, respectively, of an embodiment of a base 10 for an implant container. The base 10 may be made from a transparent or opaque plastic material such as polycarbonate. Injection molding techniques may be used in this regard.

In the present embodiment the base 10 is configured to accommodate various types of bone plate implants. It will be appreciated that in other embodiments only a single type of bone plate implant may be accommodated.

As illustrated in FIGS. 1A and 1B, the base 10 comprises multiple receiving structures 12 for bone plate implants. The receiving structures 12 are realised by recesses in the base 10 that are substantially shaped in accordance with at least a portion of a contour of the particular bone plate implant that is to be received. By having the shape of the recess correspond to at least a portion of the bone plate implant contour, the bone plate implant can be held in a defined relationship relative to the base 10. As understood herein, the defined relationship encompasses both the case in which the bone plate implant is held in a laterally fixed position relative to the base 10 and the case in which the bone plate implant can move within a well-defined range relative to the base 10. In the latter case the well-defined range may be selected such that the general orientation of the bone plate implant relative to base 10 can be maintained so as to facilitate implant removal.

In the embodiment depicted in FIGS. 1A and 1B the receiving structures 12 comprise a first type of receiving structure 12A-C and a second type of receiving structure 12D-F. The first type of receiving structure 12A-C is realized in the form of a generally elongate recess to accommodate a bone plate implant of generally elongate shape. The second type of receiving structure 12D-F is shaped so as to accommodate generally circular bone plate implants with a removable holding tab. Exemplary bone plate implants to be accommodated in the receiving structures of the first type 12A-C and the second type 12D-F, respectively, will be described in more detail below.

The receiving structures of the first type 12A-C fully overlap with the receiving structures of the second type 12D-F but do not overlap with each other. The receiving structure of the second type 12D-F, on the other hand, partially overlap with each other.

A removal canal 16 extends perpendicularly through the receiving structures 12A-C of the first type. As will be discussed in more detail below, the removal canal 16 facilitates gripping of the bone plate implants received in the receiving structures of the first type 12A-C.

As further illustrated in FIGS. 1A and 1B, the base 10 also comprises a plurality of receiving structures 14 configured to receive fixation elements for bone plate implant fixation. The receiving structures 14 are realized in the form of circular-through openings in which elongate fixation elements such as bone screws or bone pins can be held in an up-right position.

The base 10 shown in FIGS. 1A and 1B further comprises two latching hooks 18 intended to cooperate with corresponding latching openings in the lid. This co-operation between the latching hooks 18 of the base 10 and the corresponding latching openings in the lid permits to predefine one or multiple positions of the lid relative to the base 10 as will be described below.

The base 10 also comprises multiple guiding structures 20 for the lid. The guiding structures 20 are arranged so that the lid can move relative to the base 10 in a translatory manner. At the same time the guiding structures 20 prevent the lid from being lifted off.

FIG. 2 illustrates a first embodiment of a lid 30A to be used in combination with the base 10 of FIGS. 1A and 1B so as to realize a first implant container embodiment. Like the base 10, the lid 30A can also be made from a transparent or opaque plastic material using injection molding techniques.

The lid 30A of FIG. 2 has a central opening 32A and multiple lateral openings 34A. The central opening 32A has a shape that matches the combined shape of the receiving structures of the second type 12D-F in the base 10. The number and arrangement of the lateral openings 34A in the lid 30A corresponds to the number and arrangement of the receiving structures 14 for fixation elements in the base 10. As illustrated in FIG. 2, each of the lateral openings 34A has a circular shape with a diameter that slightly exceeds the maximum diameter of the fixation elements to be accommodated in the receiving structures 14 of the base 10.

On the surface of the lid 30A that faces away from the base 10 multiple gripping structures 36A, 36B, 36C are provided. The gripping structures 36A, 36B, 36C comprise surface corrugations 30A to facilitate a manual movement of the lid 30A relative to the base 10.

Moreover, the lid 30A comprises on its circumference a step-like surface structure 38. The surface structure 38 co-operates with the guiding structures 20 of the base 10 to ensure that the lid 30A cannot be lifted off from the base 10 while at the same time guiding a sliding movement of the lid 30A relative to the base 10.

FIG. 3A illustrates a second embodiment of a lid 30B that may also be used in combination with the base 10 of FIGS. 1A and 1B so as to realize a second implant container embodiment. The lid 30B of FIG. 3A generally corresponds to the lid 30A of FIG. 2 and comprises a central opening 32B for implant removal, multiple lateral openings 34B for removal of fixation elements, as well as multiple gripping structures 36A, 36B and 36C. The shape and arrangement of the central opening 32B in the lid 30B is selected to correspond with the shape and arrangement of each of the receiving structures of the first type 12A-C in the base 10 when the lid 30B is in different relative positions with respect to the base 10. In a similar manner, the shape and arrangement of the lateral openings 34B corresponds to the shape and arrangement of the receiving structures 14 for fixation elements in the base 10 when the lid 30B is in different relative positions with respect to the base 10.

Figure 3B:
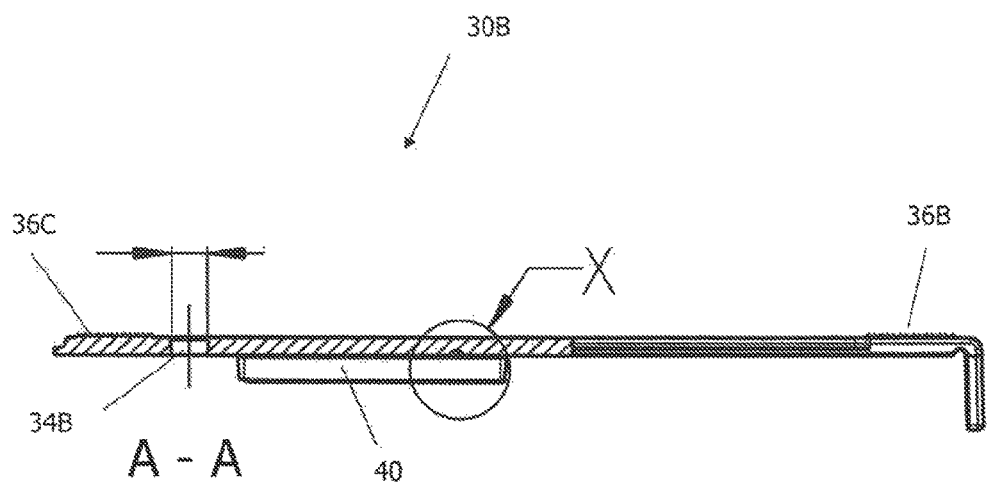
FIG. 3B shows a cross-sectional view of the lid according to FIG. 3A.

As shown in the cross-sectional view of FIG. 3B that is taken along the line A-A in FIG. 3A, the lid 30B comprises a holding member 40 arranged on a surface of the lid 30B that faces towards the base 10. The holding member 40 has the form of an elongate bar that extends from a central region of the lid 30B to the central opening 32B. The holding member 40 can also be identified in FIG. 3A and is configured to hold bone plate implants within in the receiving structures of the first type 12A-C provided in the base 10. As the bottom of those receiving structures of the first type 12A-C is arranged lower than the bottom of the receiving structures of the second type 12D-F, the holding member 40 prevents the bone plate implants accommodated in the receiving structures of the first type 12A-C from moving into the overlapping receiving structures of the second type 12D-F when the implant container is flipped over (e.g., during transport).

Figure 3C:
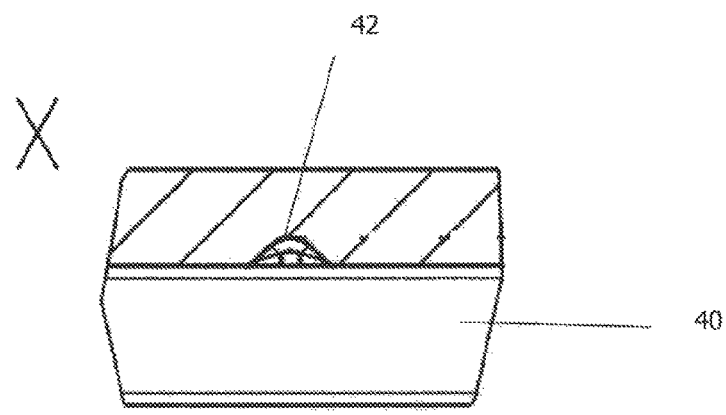
FIG. 3C shows a detail of the cross-sectional view of FIG. 3B.

FIG. 3C shows detail X of the lid 30B according to the cross-sectional view of FIG. 3B. As can be gathered from FIG. 3C, on the surface of the lid 30B facing the base 10 a latching opening 42 is provided for co-operating with one of the corresponding latching hooks 18 of the base 10. While only a single latching opening 42 is illustrated in FIG. 3C, it will be understood that multiple latching openings 42 are provided laterally along the axial extension of the lid 30B.

Figure 4A:
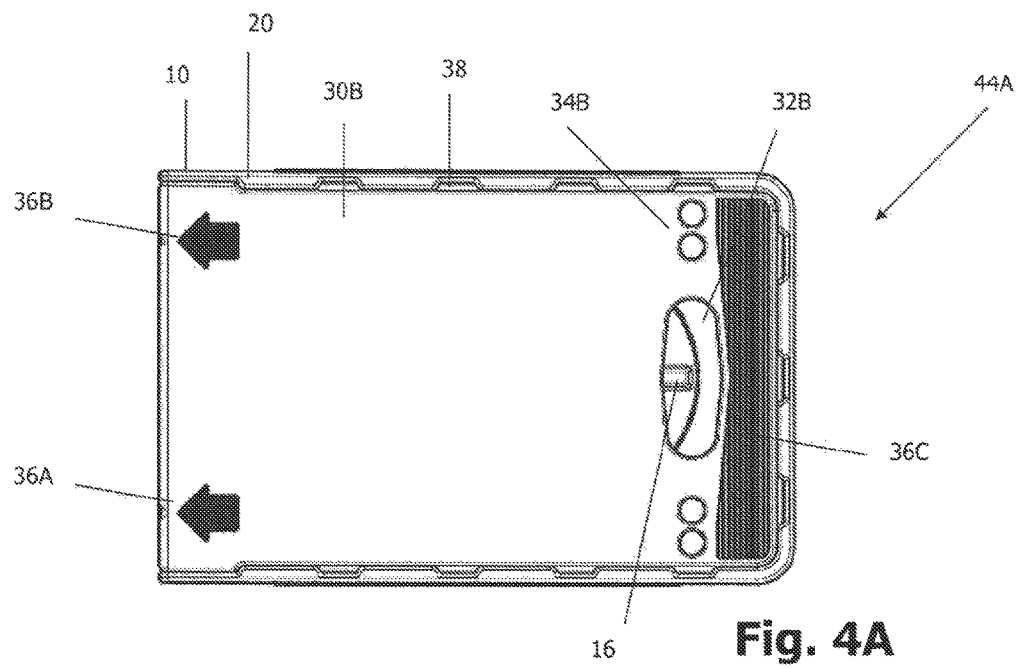
FIG. 4A shows a top view of a first embodiment of an implant container in a first relative position between base and lid.
Figure 4B:
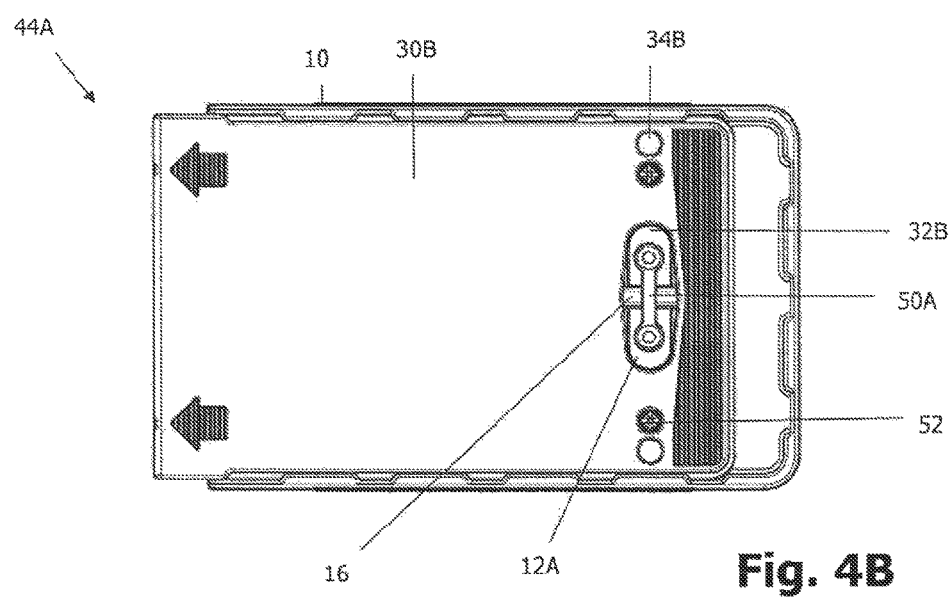
FIG. 4B shows a top view of the implant container of FIG. 4A in a second relative position between base and lid.

FIGS. 4A to 4C show a first embodiment of an implant container 44A that is assembled from the base 10 illustrated in FIGS. 1A and 1B and the lid 30B of FIGS. 3A to 3C. The implant container 44A is configured such that the lid 30B is slidingly movable between at least two (and up to four or more) positions relative to the base 10. The lid 30B can be moved relative to the base 10 as indicated by arrows that constitute the gripping structures 36A, 36B. The individual relative positions between the lid 30B and the base 10 are predefined by the latching hooks 18 of the base 10 engaging the latching openings 42 of the lid 30B.

FIG. 4A illustrates a first position of the lid 30B relative to the base 10. The first position corresponds to a closed state of the implant container 44A in which the lid 30B fully covers the receiving structures of the first type 12A-C so as to prevent implant removal.

The lid 30B can be slidingly moved from the first position illustrated in FIG. 4A to the second relative position shown in FIG. 4B. Such a movement is facilitated by the gripping structures 36A, 36B, 36C that can be gripped by a surgeon or an assistant to push the implant container 44A open.

In the open state of the container 44A (that corresponds to the second relative position between the lid 30B and the base 10) illustrated in FIG. 4B, the central opening 32B is aligned with a first one of the receiving structures of the first type 12A. Additionally, the circular openings 34B are aligned with a first row of the receiving structures 14 for fixation elements. Due to such an alignment between the openings 32B, 34B on the one hand and the receiving structures 12A, 14 on the other, the surgeon or an assistant obtains access to a bone plate implant 50 as well to associated fixation elements 52 in the form of bone screws (see FIG. 4B).

In the present embodiment, the bone plate implant 50A is an elongate bone plate with two circular screw holes at its opposite ends. Since the bone plate implant 50A is thus to be fixed to bone using a maximum of two bone screws, two bone screws 52 are accessible via the corresponding opening. It will be appreciated that the fixation elements in the form of bone screws 52 are specially adapted (e.g., regarding their length and/or diameter) to be used with the bone plate implant 50A. Therefore, the implant container 44A accommodates a complete implant system comprising the bone plate implant 50 as well as the bone screws 52 that are to be used in combination with the bone plate implant 50. In this way, it will be ensured that always the correct types and numbers of fixation elements 52 will be used in combination with the bone plate implant 50A.

With reference to FIG. 4C it will further be appreciated that the walls of the circular openings 34B can function as an axial guiding structure for a removal tool 54 (such as a screw driver) upon screw removal. Removal of the bone plate 50 is facilitated by the removal canal 16 formed below the bottom of the receiving structure of the first type 12A that accommodates the bone plate implant 50. In this regard, the canal 16 permits an easier gripping of the bone plate 50 by tweezers or forceps.

It will also be appreciated that due to the specific form of the bone plate implant 50A on the one hand on the shape of an individual receiving structure of the first type, e.g., 12A, on the other hand, the bone plate implant 50A can move within a defined range within the recess defining that receiving structure 12A. The range of movement is nonetheless restricted by the dimensioning of the recess such that the bone plate implant 50A is held in a defined relationship relative to the base 10 (i.e., it can only reach positions in which it can still be gripped via the canal 16).

Figure 4D:
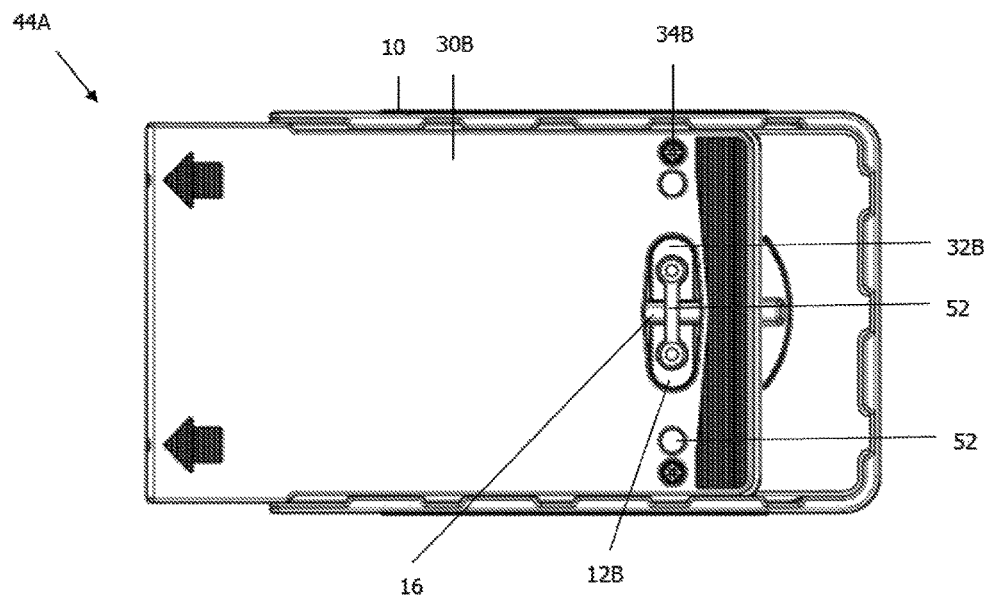
FIG. 4D shows the implant container with the lid in the third position revealing the second receiving structure.

In present embodiment of the base 10, three receiving structures of the first type 12A-C are provided in the base 10. For this reason, the implant container 44A can be filled with up to three bone plate implants 50A of the type illustrated in FIGS. 4B and 4C. Accordingly, once the bone implant 50A accessible via the first receiving structure of the first type 12A has been removed, the lid 30B may be pushed to a third position relative to the base 10 in which the bone plate implant accommodated in the next receiving structure of the first type 12B becomes accessible (see FIGS. 1A and 4D) for removal together with the associated fixation elements, and so on.

Figure 5C:
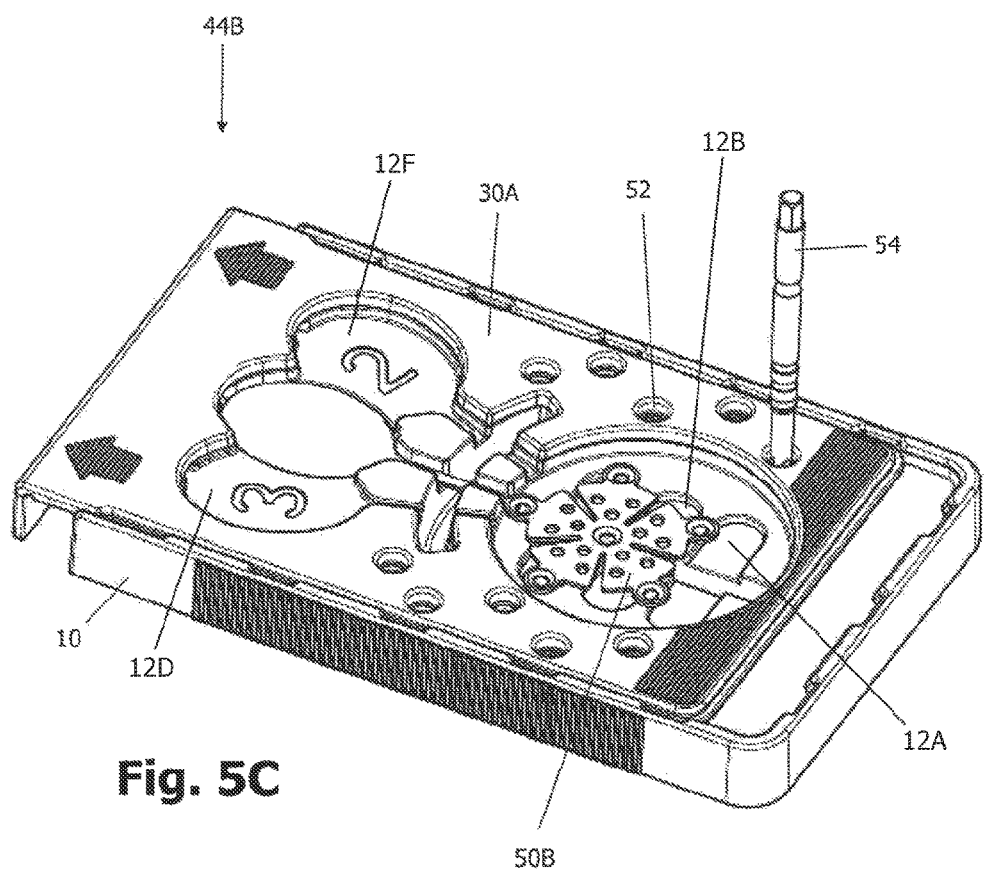
FIG. 5C shows a perspective view of the implant container according to FIG. 5B in a surgical scenario with a removal tool.

FIGS. 5A to 5C illustrate a second embodiment of an implant container 44B that is assembled from the base 10 of FIGS. 1A and 1B and the lid 32A of FIG. 2. As shown in FIGS. 5A and 5B, the lid 30A can be moved relative to the base from a first position (i.e., from a closed state) to a second position (i.e., to an open state). In the closed state, the lid 30A partially covers the receiving structures of the second type 12D-F and also a bone plate implant 50B received therein. In the closed state, the bone plate implant 50B is thus prevented from falling out of the implant container 44B even if the implant container 44B is flipped over.

In the open state of the implant container 44B illustrated in FIG. 5B, the bone plate implant 50B can be removed from the corresponding receiving structure of the second type 12D-F via the central opening 32A. At the same time, the surgeon or an assistant obtains access to multiple fixation elements 52 (which can be realized in the form of bone screws) via the lateral openings 34A.

As can be gathered from FIG. 5B, the bone plate implant 50B is a burr hole plate with a removable holding tab. The burr hole plate is to be fixed to bone using five bone screws, and exactly five bone screws are accessible via the corresponding openings 34A provided in the lid 30A. Bone screw removal is again facilitated by the openings 34A functioning as axial guiding structure for the removal tool 54 as illustrated in FIG. 5C. It will be appreciated that at least a second bone plate implant 50B of the type illustrated in FIGS. 5A to 5C may be accommodated within the base 10 together with five more bone screws 52.

Figure 6:
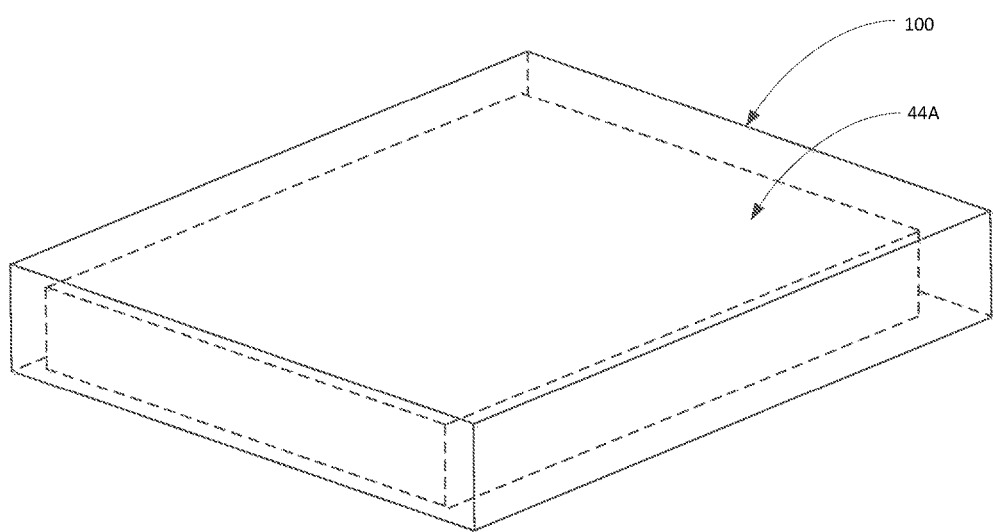
FIG. 6 shows packaging for the implant container shown in FIG. 4A.

The implant container 44A, 44B of the above embodiments may be packaged in a sterile manner. In one example shown in FIG. 6, implant container 44A is packaged in a packaging member in the form of a blister pack 100. In another example, the implant container 44A, 44B may be packaged in a blister pack as generally known from GB 2 418 421 A. If required, the sterile packaging may additionally comprise a bag or any other packaging structure surrounding the blister pack.

As has come apparent from the description of exemplary embodiments, the implant container system presented herein facilitates the handling of bone plate implants in a surgical environment. In certain configurations, all the components of an implant system (including at least one bone plate implant and at least one associated fixation element) can be provided in a single implant container. Moreover, in certain configurations, all components of such an implant system that are required for a specific surgical procedure may be made available to a surgeon together. In certain configurations, a single base may be used in combination with different types of bone plate implants and different types of lids.

While the invention has been described with respect to particular embodiments, those skilled in the art will recognize that the present invention is not limited to the specific embodiments described and illustrated herein. It is to be understood that this disclosure is only illustrative. Accordingly, it is intended that the invention be limited only by the scope of the claims appended hereto.

The invention claimed is:

1. An implant container for receiving at least one bone plate implant, the implant container comprising:
    a base having a first receiving structure configured to receive at least one first bone plate implant so that the first bone plate implant is held in a defined relationship relative to the base, the first receiving structure partially defined by a first surface recessed relative to a top surface of the base and the base including a second surface recessed relative to the first surface;
    a first lid having a first opening and being movable relative to the base from a first position to at least a second position, wherein in the first position the first lid covers the first receiving structure at least partially so as to prevent removal of the first bone plate implant and in the second position the first lid provides access to the first receiving structure via the first opening so as to permit implant removal; and
    the base having at least one fixation element receiving structure, wherein in the first position the first lid covers the fixation element receiving structure at least partially so as to prevent access to the fixation element receiving structure and in the second position the first lid provides access to the fixation element receiving structure through a second opening in the first lid.

2. The implant container of claim 1, wherein the base further comprises at least one second receiving structure configured to receive at least one second bone plate implant so that the second bone plate implant is held in a defined relationship relative to the base.

3. The implant container of claim 2, wherein the first receiving structure and the second receiving structure overlap at least partially.

4. The implant container of claim 2, wherein in the second position the first lid provides access to the second receiving structure via the first opening so as to permit removal of an implant when the implant is disposed in the second receiving structure.

5. The implant container of claim 2, wherein the first lid is movable relative to the base from the first position to a third position different from the second position, wherein in the first position and in the second position the first lid covers the second receiving structure at least partially so as to prevent removal of an implant when the implant is disposed in the second receiving structure and in the third position the first lid provides access to the second receiving structure via the first opening so as to permit removal of the implant.

6. The implant container of claim 2, wherein the at least one fixation element receiving structure is configured to receive a fixation element for bone plate implant fixation.

7. The implant container of claim 6, wherein the second opening is dimensioned so that walls in the first lid defining the second opening act as an axial guiding structure for a removal tool upon removal of the fixation element by the removal tool.

8. The implant container of claim 6, wherein the base comprises a number of fixation element receiving structures and the first lid comprises a number of second openings that correspond to the number of a plurality of fixation elements needed for bone plate implant fixation using the first bone plate implant.

9. The implant container of claim 1, wherein the first lid is slidably guided relative to the base.

10. The implant container of claim 1, wherein at least the first receiving structure is a recess in the base, wherein the recess is substantially shaped in accordance with at least a portion of a contour of the first bone plate implant.

11. The implant container of claim 1, further comprising a latching mechanism that predefines at least the second position of the first lid relative to the base.

12. The implant container of claim 1, further comprising a packaging member configured to package the base and the first lid in a sterile manner, the base configured to support the first bone plate implant therein.

13. The implant container of claim 12, wherein the packaging member comprises a blister pack.

14. The implant container of claim 1, further comprising at least the first bone plate implant.

15. The implant container of claim 1, wherein the first lid comprises at least one of:
a gripping structure arranged on a surface of the first lid that faces away from the base or laterally arranged on the first lid, the gripping structure being configured to facilitate a transfer of the first lid from the first position to at least the second position; and
a holding member arranged on a surface of the first lid that faces toward the base, the holding member being configured to hold at least the first bone plate implant in at least the first receiving structure.

16. An implant container for receiving a plurality of bone implants comprising:
a base having a plurality of first receptacles configured to hold a bone plate implant, the plurality of first receptacles spaced from a top surface of the base and spaced along a longitudinal extent of the base, the base having a first latching element thereon,
a lid slidably mounted on the base adjacent the top surface, the lid having a plurality of second latching elements for engaging the first latching element, the second latching elements spaced along a longitudinal extent of the lid at distances equal to the spacing of the first receptacles along the longitudinal extent of the base, the lid having a first opening positionable over each of the first receptacles when the first latching element engages one of the plurality of second latching elements; and
the base having at least one second receptacle configured to receive a fixation element, wherein in a first position the first lid covers one of the at least one second receptacle at least partially so as to prevent access to the one of the at least one second receptacle and in a second position the first lid provides access to the one of the at least one second receptacle through a second opening in the first lid,
wherein when the lid is slidably mounted on the base and first latching element engages with one of the plurality of second latching elements, physical engagement between the base and the lid occurs between the top surface of the base and a surface of the lid facing the top surface.

17. The implant container as set forth in claim 16 wherein the base comprises a plurality of holders configured to hold bone screws and the lid has a plurality of openings located such that a bone screw can be removed from a holder through the lid openings when the first latching element engages one of the second latching elements.

18. The implant container of claim 16 wherein the lid comprises a gripping structure arranged on a surface of the lid that faces away from the base, the gripping structure being configured to facilitate a transfer of the lid from the first position to at least the second position; and
a holding member arranged on a surface of the lid that faces toward the base, the holding member being configured to hold at least the bone plate implant in at least the receiving structure.

19. An implant container for receiving a plurality of bone plates, the bone plates having apertures for receiving bone screws, the implant container comprising:
a base having a plurality of first support structures located between a bottom surface of the base and an open top portion of the base, each first support structure capable of supporting one of a plurality of bone plates, the plurality of first support structures spaced along a longitudinal extent of the base;
the base further comprising a plurality of second support structures associated with each first support structure capable of supporting a plurality of bone screws; and
a lid having a first and a second opening therein slidably mounted on the base adjacent the open top portion thereof, the lid having a first position wherein the first and second openings in the lid are positioned to cover the first and second support structures to prevent removal of any of the plurality of bone plates or bone screws, the first and second openings in the lid positionable over each of the plurality of first support structures and second support structures, in series, as the lid is slid along the top portion along the longitudinal extent of the base from the first position along the longitudinal extent of the base to a second position wherein the first and second openings, respectively are over the first and second support structures to allow removal of a bone plate and bone screw and wherein the lid, once slid into the first or second position, remains in the same position without holding the base or the lid.

20. The implant container of claim 19 wherein the number of second support structures equals the number of bone screw receiving apertures in the bone plate received in the first support structure.

21. The implant container of claim 19 wherein the lid is movable relative to the base from the first position to a third position different from the second position, wherein in the first position and in the second position the lid covers the second support structure at least partially so as to prevent removal of the second bone plate implant and in the third position the first lid provides access to the second support structure via the first opening so as to permit of the second bone plate implant removal.

22. An implant container for receiving at least one bone plate implant, the implant container comprising:
 a base having a first receiving structure configured to receive at least one first bone plate implant so that the first bone plate implant is held in a defined relationship relative to the base, the first receiving structure partially defined by a first surface recessed relative to a top surface of the base and the base including a second surface recessed relative to the first surface;
 a first lid having a first opening and the first lid being movable relative to the base from a first position to at least a second position, wherein in the first position the first lid covers the first receiving structure at least partially so as to prevent removal of the first bone plate implant and in the second position the first lid provides access to the first receiving structure via the first opening so as to permit removal of the first bone plate implant;
 the base having at least one second receiving structure configured to receive at least one second bone plate implant so that the second bone plate implant is held in a defined relationship relative to the base; and
 wherein the first lid is movable relative to the base from the first position to a third position different from the second position, wherein in the first position and in the second position the first lid covers the second receiving structure at least partially so as to prevent removal of the second bone plate implant and in the third position the first lid provides access to the second receiving structure via the first opening so as to permit removal of the second bone plate implant.

* * * * *